United States Patent [19]

Brooks et al.

[11] Patent Number: 5,326,883

[45] Date of Patent: Jul. 5, 1994

[54] OXIME ETHER DERIVATIVES HAVING LIPOXYGENASE INHIBITORY ACTIVITY

[75] Inventors: Dee W. Brooks, Libertyville; Andrew O. Stewart, Wildwood, both of Ill.; Robert G. Maki, Kenosha, Wis.

[73] Assignee: Abbott Laboratories, Abbott Park, Ill.

[21] Appl. No.: 992,388

[22] Filed: Dec. 18, 1992

[51] Int. Cl.$^5$ .................. C07D 307/58; C07D 333/32; A61K 31/34; A61K 31/38
[52] U.S. Cl. ................................. 549/65; 549/479; 549/55; 514/473; 514/427; 514/640; 562/623; 548/561
[58] Field of Search ................. 548/561; 549/65, 55, 549/479; 514/441, 473, 640

[56] References Cited

U.S. PATENT DOCUMENTS

| | | | |
|---|---|---|---|
| 4,144,245 | 3/1979 | Cale | 548/551 |
| 5,169,854 | 12/1992 | Brooks et al. | 549/479 |
| 5,240,958 | 8/1993 | Campion et al. | 549/65 |

*Primary Examiner*—David B. Springer
*Attorney, Agent, or Firm*—Jerry F. Janssen

[57] ABSTRACT

The present invention provides certain substituted oxime ether compounds which inhibit lipoxygenase enzyme activity and are useful in the treatment of allergic and inflammatory disease states. The compounds of this invention have the structure

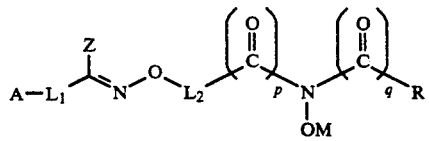

where M is hydrogen, a pharmaceutically acceptable cation, or a pharmaceutically acceptable metabolically cleavable group; p and q are independently zero or one, with the provisos that (i) p and q may not both be the same; (ii) when p is one and q is zero, R is selected from the group consisting of hydrogen, straight or branched alkyl of from one to twelve carbon atoms, and cycloalkyl of from three to eight carbon atoms; and (iii) when p is zero and q is one, R is selected from the group consisting of hydrogen, alkyl of from one to twelve carbon atoms, cycloalkyl of from three to eight carbon atoms, and —$NR_1R_2$.

$L_1$ is a direct bond or is selected from the group consisting of alkyl of from one to six carbon atoms, alkylenyl, of from one to six carbon atoms, and alkynyl of from two to six carbon atoms; $L_2$ is a direct bond or is alkyl of from one to six carbon atoms; Z is selected from the group consisting of hydrogen, alkyl of from one to six carbon atoms, and halosubstituted alkyl of from one to six carbon atoms; and A is optionally substituted carbocyclic or heterocyclic aryl, arylalkyl, or aryloxy.

4 Claims, No Drawings

OXIME ETHER DERIVATIVES HAVING LIPOXYGENASE INHIBITORY ACTIVITY

TECHNICAL FIELD

This invention relates to compounds having biological activity to inhibit lipoxygenase enzymes, to pharmaceutical compositions comprising these compounds, and to a medical method of treatment. More particularly, this invention concerns certain substituted oxime ether compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the first dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, converting them to 1-hydroperoxytrans,cis-2,4-pentadienes. Arachidonic acid, the 5-lipoxygenase substrate which leads to leukotriene products, is found in very low concentrations in mammalian cells and must first be hydrolyzed from membrane phospholipids through the actions of phospholipases in response to extracellular stimuli. The initial product of 5-lipoxygenase action on arachidonate is 5-HPETE which can be reduced to 5-HETE or converted to LTA4. This reactive leukotriene intermediate is enzymatically hydrated to LTB4 or conjugated to the tripeptide glutathione to produce LTC4. LTA4 can also be hydrolyzed nonenzymatically to form two isomers of LTB4. Successive proteolytic cleavage steps convert LTC4 to LTD4 and LTE4. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the bisynthesis of all the leukotrienes and therefore inhibition of this enzyme provides an approach to limit the effects of all the products of this pathway. Compounds which inhibit 5-lipoxygenase are thus useful in the treatment of disease states such as those listed above in which the leukotrienes play an important role.

U.S. Pat. No. 4,738,986 to Kneen, et al. discloses and claims N-(3-phenoxycinnamyl)acetohydroxamic acid, its salts and related compounds having utility for inhibiting lipoxygenase and cyclooxygenase enzymes.

European Patent Application 0 299 761 to Salmon, et al. discloses and claims certain (substituted phenoxy)-phenylalkenyl hydroxamic acids and their salts which are useful as agents for inhibiting lipoxygenase and cyclooxygenase activity.

SUMMARY OF THE INVENTION

In its principal embodiment, the present invention provides certain substituted oxime ether compounds which inhibit lipoxygenase enzyme activity and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The compounds of this invention have the structure

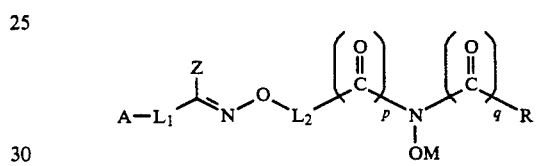

Included within the scope of the present invention are also pharmaceutically acceptable salts of compounds of the above structure.

In the generic chemical structure shown above, M is selected from the group consisting of hydrogen, a pharmaceutically acceptable cation, and a pharmaceutically acceptable metabolically cleavable group.

The subscripts p and q are independently zero or one, with the provisos that (i) p and q may not both be the same; (ii) when p is one and q is zero, R is selected from the group consisting of hydrogen, straight or branched alkyl of from one to twelve carbon atoms, and cycloalkyl of from three to eight carbon atoms; and (iii) when p is zero and q is one, R is selected from the group consisting of hydrogen, alkyl of from one to twelve carbon atoms, cycloalkyl of from three to eight carbon atoms, and $-NR_1R_2$ wherein $R_1$ is selected from the group consisting of hydrogen, alkyl of from one to six carbon atoms, hydroxyalkyl of from one to six carbon atoms, and alkoxyalkyl in which the alkoxy portion and the alkyl portion each contain, independently, from one to six carbon atoms; and $R_2$ is selected from the group consisting of hydrogen, hydroxy, alkyl of from one to six carbon atoms, hydroxyalkyl of from one to six carbon atoms, alkoxyalkyl in which the alkoxy portion and the alkyl portion each contain, independently, from one to six carbon atoms, alkanoyl of from two to eight carbon atoms, alkyl(carbocyclic aryl) in which the alkyl portion contains from one to six carbon atoms, and optionally substituted (carbocyclic aryl).

The group $L_1$ is a direct bond or is selected from the group consisting of alkyl of from one to six carbon atoms, alkylenyl, of from one to six carbon atoms, and alkynyl of from two to six carbon atoms.

$L_2$ is a direct bond or is alkyl of from one to six carbon atoms.

Z is selected from the group consisting of hydrogen, alkyl of from one to six carbon atoms, and halosubstituted alkyl of from one to six carbon atoms.

A is selected from the group consisting of (a) alkyl of from five to twenty carbon atoms; (b) cycloalkyl of from three to eight carbon atoms; (c) optionally substituted carbocyclic aryl; (d) optionally substituted (carbocyclic aryl)alkyl in which the alkyl portion contains from one to six carbon atoms; (e) optionally substituted (carbocyclic aryl)cycloalkyl in which the cycloalkyl portion contains from three to eight carbon atoms and the alkyl portion contains from one to six carbon atoms; (f) optionally substituted carbocyclic aryloxyalkyl in which the alkyl portion contains from one to six carbon atoms; (g) optionally substituted (carbocyclic aryl)alkoxyalkyl in which the alkoxyl and alkyl portions independently contain rom one to six carbon atoms; (h) optionally substituted carbocyclic arylthioalkyl in which the thioalkyl portion may contains from one to six carbon atoms; (i) optionally substituted carbocyclic arylaminoalkyl in which the alkyl portion contains from one to six carbon atoms; (j) optionally substituted benzo[b]furyl; (k) optionally substituted thienyl; (l) optionally substituted furanyl; (m) optionally substituted pyridyl; (n) optionally substituted pyrrolyl; (o) optionally substituted quinolinyl; (p) optionally substituted 2- or 3-benzo[b]thienyl; and (q) optionally substituted indolyl.

In the above definitions for the group A, the optional substituents on the carbocyclic aryl and heterocyclic aryl groups are selected from (1) alkyl of from one to six carbon atoms, (2) haloalkyl of from one to six carbon atoms, (3) alkoxy of from one to twelve carbon atoms, (4) halogen; (5) phenyl or naphthyl, in turn optionally substituted with alkyl of from one to six carbon atoms, haloalkyl of from one to six carbon atoms, alkoxy of from one to six carbon atoms, halogen; (6) phenoxy or naphthyloxy, in turn optionally substituted with alkyl of from one to six carbon atoms, haloalkyl of from one to six carbon atoms, alkoxy of from one to six carbon atoms, halogen; (7) phenylthio, optionally substituted with alkyl of from one to six carbon atoms, haloalkyl of from one to six carbon atoms, alkoxy of from one to six carbon atoms, halogen; (8) phenylalkyl, where the alkyl contains from one to six carbon atoms, and the phenyl group is optionally substituted with alkyl of from one to six carbon atoms, haloalkyl of from one to six carbon atoms, alkoxy of from one to six carbon atoms, halogen; (9) pyridyl, optionally substituted with alkyl of from one to six carbon atoms, haloalkyl of from one to six carbon atoms, alkoxy of from one to six carbon atoms, halogen; (10) pyridyloxy, optionally substituted alkyl of from one to six carbon atoms, haloalkyl of from one to six carbon atoms, alkoxy of from one to six carbon atoms, halogen; (11) pyridylalkyl, where the alkyl is from one to six carbon atoms, and the pyridyl group is optionally substituted with alkyl of from one to six carbon atoms, haloalkyl of from one to six carbon atoms, alkoxy of from one to six carbon atoms, halogen; (12) quinolyl, optionally substituted with alkyl of from one to six carbon atoms, haloalkyl of from one to six carbon atoms, alkoxy of from one to six carbon atoms, halogen; (13) quinolylalkyl, where the alkyl is from one to six carbon atoms, and the quinolyl group is optionally substituted with alkyl of from one to six carbon atoms, haloalkyl of from one to six carbon atoms, alkoxy of from one to six carbon atoms, halogen; and (14) quinolylalkoxy, where the alkoxy group contains from one to six carbon atoms, and the quinolyl group is optionally substituted with alkyl of from one to six carbon atoms, haloalkyl of from one to six carbon atoms, alkoxy of from one to six carbon atoms, halogen.

In another embodiment, the present invention provides pharmaceutical compositions which comprise a therapeutically effective amount of compound as defined above in combination with a pharmaceutically acceptable carrier.

In a still further embodiment, the present invention provides a method of inhibiting leukotriene biosynthesis in a host mammal in need of such treatment comprising administering to a mammal in need of such treatment a therapeutically effective amount of a compound as defined above.

DETAILED DESCRIPTION OF THE INVENTION

DEFINITIONS OF TERMS

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The term "cycloalkyl" denotes a monovalent group derived from a monocyclic or bicyclic saturated carbocyclic ring compound by the removal of a single hydrogen atom. Examples include cyclopropyl, cyclobutyl, cycopentyl, cyclohexyl, bicyclo[2.2.1]heptanyl, and bicyclo[2.2.2]octanyl.

The term "cycloalkylene" refers to a divalent group derived from a saturated carbocyclic hydrocarbon by the removal of two hydrogen atoms, for example cyclopentylene, cyclohexylene, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxyalkyl" refers to an alkoxy group, as defined above, attached through an alkylene group to the parent molecular moiety.

The term "alkylthio" refers to an alkyl group, as defined above, attached to the parent molecular moiety through a sulfur atom and includes such examples as methylthio, ethylthio, propylthio, n-, sec- and tert-butylthio and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "alkenylene" denotes a divalent group derived from a straight or branched chain hydrocarbon containing at least one carbon-carbon double bond. Examples of alkenylene include —CH=CH—, —CH2CH=CH—, —C(CH3)=CH—, —CH2CH=CHCH2—, and the like.

The term "alkynyl" refers to a divalent group derived by the removal of two hydrogen atoms from a straight or branched chain acyclic hydrocarbon group containing a carbon-carbon triple bond.

The term "alkanoyl" represents an alkyl group, as defined above, attached to the parent molecular moiety through a carbonyl group. Alkanoyl groups are exemplified by acetyl, propionyl, butanoyl and the like.

The term "carbocyclic aryl" denotes a monovalent carbocyclic ring group derived by the removal of a single hydrogen atom from a monocyclic or bicyclic fused or non-fused ring system obeying the "4 n+2 p electron" or Huckel aromaticity rule. Examples of carbocyclic aryl groups include phenyl, 1-and 2-naphthyl, biphenylyl and the like.

The term "(carbocyclic aryl)alkyl" refers to a carbocyclic ring group as defined above, attached to the parent molecular moiety through an alkylene group. Representative (carbocyclic aryl)alkyl groups include phenylmethyl or benzyl, phenylethyl, phenylpropyl, 1-naphthylmethyl, and the like.

The term "carbocyclic aryloxyalkyl" refers to a carbocyclic aryl group, as defined above, attached to the parent molecular moiety through an oxygen atom and thence through an alkylene group. Such groups are exemplified by phenoxymethyl, 1- and 2-naphthyloxymethyl, phenoxyethyl and the like.

The term "(carbocyclic aryl)alkoxyalkyl" denotes a carbocyclic aryl group as defined above, attached to the parent molecular moiety through an alkoxyalkyl group. Representative (carbocyclic aryl)alkoxyalkyl groups include phenylmethoxymethyl, phenylethoxymethyl, 1- and 2-naphthylmethoxyethyl, and the like.

"Carbocyclic arylthioalkyl" represents a carbocyclic aryl group as defined above, attached to the parent molecular moiety through a sulfur atom and thence through an alkylene group and are typified by phenylthiomethyl, 1-and 2-naphthylthioethyl and the like.

The term "carbocyclic arylaminoalkyl" refers to a carbocyclic aryl group as defined above, attached to the parent molecular moiety through a -NH-alkylene-group and is exemplified by phenylaminomethyl, phenylaminoethyl, 1- and 2-naphthylaminomethyl and the like.

The term "metabolically cleavable group" denotes a group which is cleaved in vivo to yield the parent molecule of the structural formulae indicated above wherein M is hydrogen. Examples of metabolically cleavable groups include —COR, —COOR, —CONRR and —CH2OR radicals where R is selected independently at each occurrence from alkyl, trialkylsilyl, carbocyclic aryl or carbocyclic aryl substituted with one or more of C1–C4 alkyl, halogen, hydroxy or C1–C4 alkoxy. Specific examples of representative metabolically cleavable groups include acetyl, methoxycarbonyl, benzoyl, methoxymethyl and trimethylsilyl groups.

PREFERRED EMBODIMENTS

Preferred compounds of the present invention are those having the structure

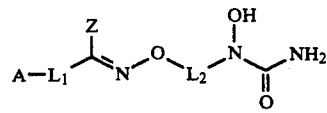

where the values of A, $L_1$, $L_2$, and Z are as defined above. Particular compounds falling within the scope of the present invention include, but are not limited to:

1-(benzo[b]thien-2-yl)ethyloximyl-O-2-ethyl-N-hydroxyurea;

hexyloximyl-O-2-ethyl-N-hydroxyurea;

1-(4-chlorobenzyl)-pyrro-2-ylmethyloximyl-O-2-ethyl-N-hydroxyurea;

3-(4-fluorophenoxy)phenylmethyloximyl-O-2-ethyl-N-hydroxyurea;

5-(4-fluorophenoxy)fur-2-ylmethyloximyl-O-2-ethyl-N-hydroxyurea;

5-(4-fluorophenoxy)fur-2-ylmethyl-Z-oximyl-O-2-(1-methyl)ethyl-N-hydroxyurea;

5-(4-fluorophenoxy)fur-2-ylmethyl-E-oximyl-O-2-(1-methyl)ethyl-N-hydroxyurea;

5-(4-fluorophenoxy)fur-2-ylmethyl-E-oximyl-O-2-(2-methyl)ethyl-N-hydroxyurea;

5-(4-fluorophenoxy)fur-2-ylmethyl-Z-oximyl-O-2-(2-methyl)ethyl-N-hydroxyurea;

5-(phenylthio)fur-2-ylmethyloximyl-O-2-ethyl-N-hydroxyurea;

4-(4-fluorophenyl)cyclohex-1-yloximyl-O-2-ethyl-N-hydroxyurea;

6-methoxynaphth-2-yl(2-methyl)ethyloximyl-O-2-ethyl-N-hydroxyurea;

N-methyl-(1amino-4-sec-butylphenyl)-N-propyloximyl-O-2-ethyl-N-hydroxyurea;

3-(2-pyridinyloxy)phen-1-ylmethyloximyl-O-2-ethyl-N-hydroxyurea;

5-(2,4-difluorophen-1-yl)fur-2-ylmethyloximyl-O-2-ethyl-N-hydroxyurea;

5-(3-pyridinyl)fur-2-ylmethyloximyl-O-2-ethyl-N-hydroxyurea;

5-(2,4-difluorophen-1-yl)thiophen-2-ylmethyloximyl-O-2-ethyl-N-hydroxyurea;

5-(4-fluorophenoxy)pyridin-2-ylmethyloximyl-O-2-ethyl-N-hydroxyurea;

4-fluoro-1-benzo[b]fur-2-ylmethyloximyl-O-2-ethyl-N-hydroxyurea;

1-quinolylmethyloximyl-O-2-ethyl-N-hydroxyurea;

5-(4-fluorophenylmethyl)fur-2-ylmethyloximyl-O-2-ethyl-N-hydroxyurea;

5-(4-fluorophenylmethyl)thiophen-2-ylmethyloximyl-O-2-ethyl-N-hydroxyurea;

and compounds having the names above wherein the N-hydroxy hydrogen atom is replaced by a pharmaceutically acceptable cation, or a pharmaceutically acceptable metabolically cleavable group.

Certain compounds of this invention may exist in either cis or trans or E or Z isomers with respect to the oxime geometry and in addition to stereoisomeric forms by virtue of the presence of one or more chiral centers. The present invention contemplates all such geometric and stereoisomers, including R- and S-enantiomers, diastereomers, and cis/trans or E/Z mixtures thereof as falling within the scope of the invention. If a particular enantiomer is desired, it may be prepared by asymmetric synthesis or by derivatization with a chiral auxiliary and the resulting diastereomeric mixture is separated and the auxiliary group cleaved to provide the pure desired enantiomers.

LIPOXYGENASE INHIBITION DETERMINATION

Inhibition of leukotriene biosynthesis was evaluated in an assay, involving calcium ionophore-induced LTB4 biosynthesis expressed human whole blood. Human heparinized whole blood was preincubated with test compounds or vehicle for 15 min at 37° C. followed by calcium ionophore A23187 challenge (final concentration of 8.3 $\mu$M) and the reaction terminated after 30 min by adding two volumes of methanol containing prostaglandin B2 as an internal recovery standard. The methanol extract was analyzed for LTB4 using a commercially available radioimmunoassay.

The compounds of this invention inhibit leukotriene biosynthesis as illustrated in Table 1.

TABLE 1

In Vitro Inhibitory Potencies of Compounds of this Invention Against 5-Lipoxygenase from Stimulated LTB4 Formation in Human Whole Blood

| Example | $IC_{50}$ ($10^{-6}$M) |
| --- | --- |
| 1 | 0.1 |
| 2 | 0.1 |
| 3 | 0.16 |
| 4 | 0.1 |
| 5 | 88% @ 0.1 |
| 6 | 61% @ 0.1 |
| 7 | 49% @ 0.1 |
| 8 | 0.14 |
| 9 | 0.1 |
| 10 | 0.1 |

Inhibition of Leukotriene Biosynthesis

Inhibition of the biosynthesis of leuktrienes in vivo after oral administration of compound was determined using a rat peritoneal anaphylaxis model in a similar manner as that described by Young and coworkers (Young, P. R.; Dyer, R. D.; Carter, G. W. Fed. Proc., Fed. Am. Soc. Exp. Biol. 1985, 44, 1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. From the results of this assay it is demonstrated that compounds of this invention are orally effective in preventing the in vivo biosynthesis of leukotrienes. The results are presented in Table 2.

TABLE 2

| Example | % Inhibition of Leukotrienes Oral Dose at 30 $\mu$mol/kg |
| --- | --- |
| 6 | 70 |
| 7 | 56 |
| 9 | 64 |

PHARMACEUTICAL COMPOSITIONS

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

PREPARATION OF COMPOUNDS OF THIS INVENTION

The compounds of this invention can be prepared by a variety of synthetic routes. Representative procedures are outlined as follows.

Scheme 1 illustrates a general route for the preparation of hydroxamic acid compounds of this invention involving the convergent assembly of an oxime ether intermediate V which is then functionalized with a hydroxamic acid group to provide the desired products VI. The requisite hydroxylamine intermediate III is prepared by known methods, for example, O-alkylation of N-hydroxyphthalimide with the requisite intermediate I provides the adduct II which is then cleaved to release the desired alkoxylamine derivative III. The requisite carbonyl intermediate IV is then condensed with the alkoxyamine III to provide the key intermediate oxime ether V. The oxime ether intermediate V is then converted to the desired hydroxamic acid VI by known methods.

Scheme 1

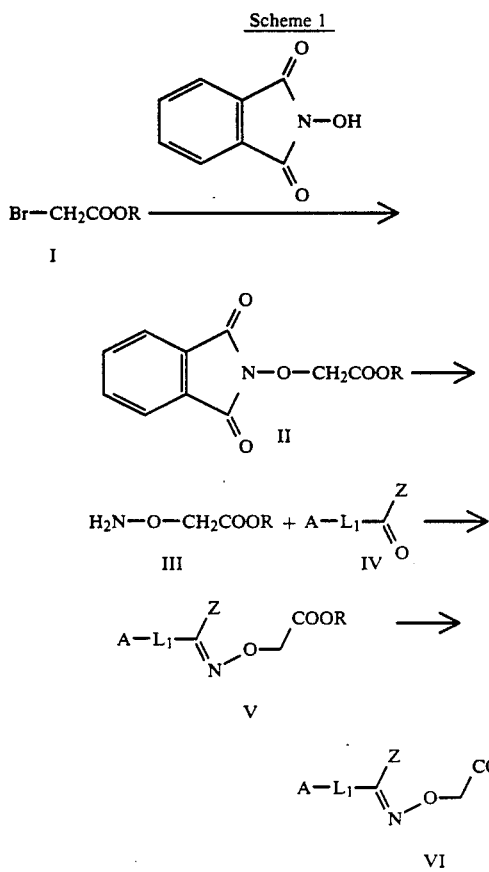

Scheme 2 illustrates a general route for the preparation of N-hydroxyurea compounds of this invention. Reduction of the ester function in intermediate V provides the hydroxy derivative VII which is treated with triphenylphosphine, diethylazodicarboxylate, and a N-O-bis-alkoxycarbonyl reagent VIII to provide the adduct IX. The bis-alkoxycarbonyl is transformed by known methods to the intermediate hydroxylamine X which is then converted to the desired N-hydroxurea compounds XI by treatment with TMS-isocyanate, HCNO, or substituted isocyanates (R-CNO).

Scheme 2

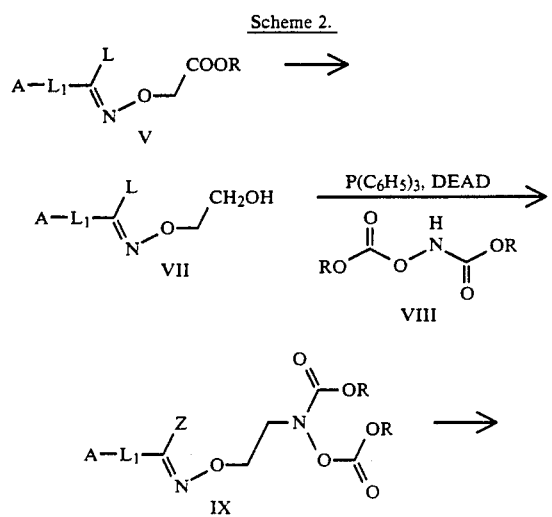

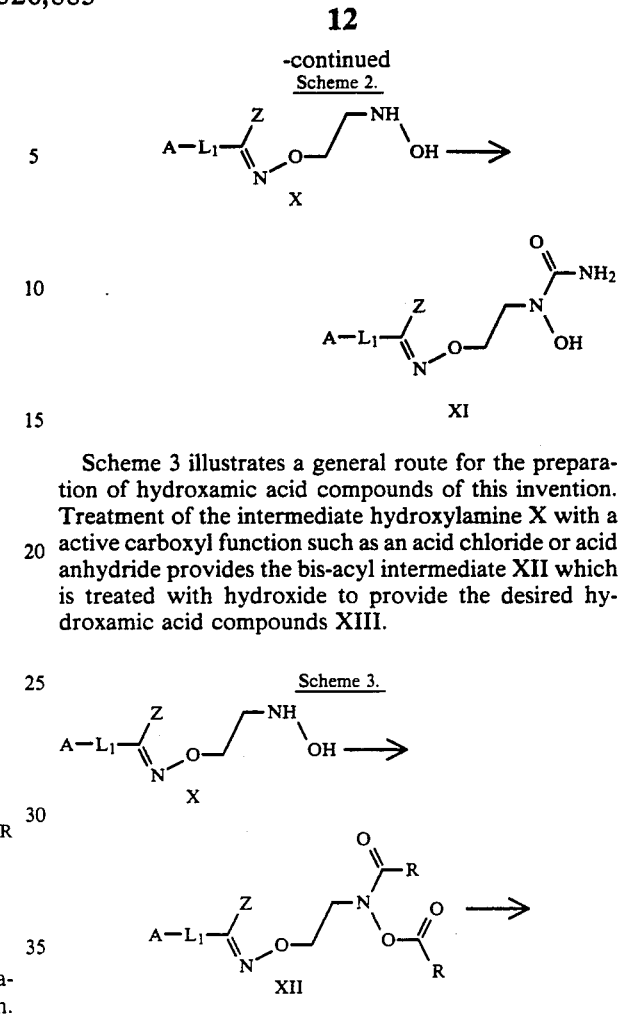

Scheme 3 illustrates a general route for the preparation of hydroxamic acid compounds of this invention. Treatment of the intermediate hydroxylamine X with a active carboxyl function such as an acid chloride or acid anhydride provides the bis-acyl intermediate XII which is treated with hydroxide to provide the desired hydroxamic acid compounds XIII.

Scheme 3

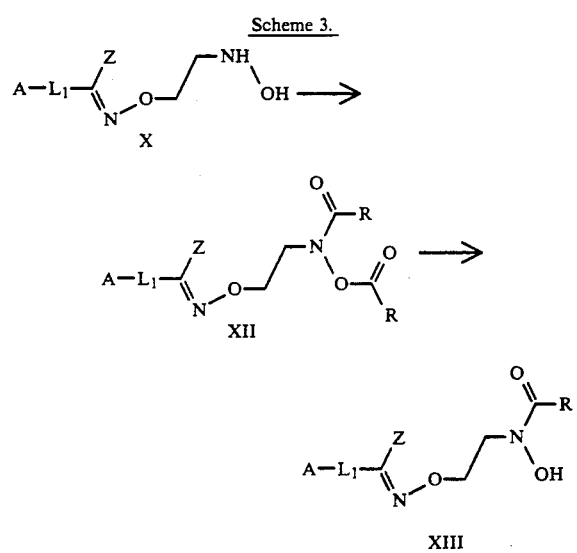

Scheme 4 illustrates an alternative route to the N-hydroxyurea oxime ether compounds. Treatment of the hydroxy derivative VII with triphenylphosphine, diethylazodicarboxylate, and N-O-bis-phenoxycarbonyl XIV to provide the adduct XV which is reacted with ammonia, ammonium hydroxide, or a primary amine to provide the desired N-hydroxyurea compound XVI.

Scheme 4

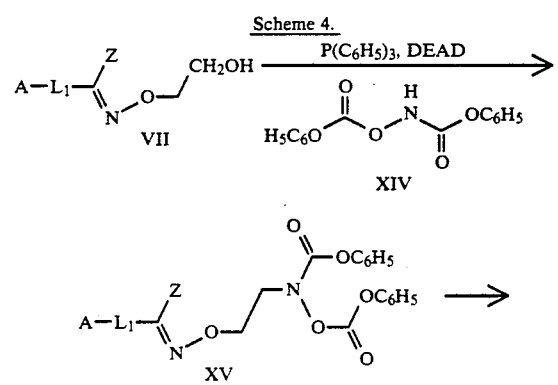

-continued
Scheme 4.

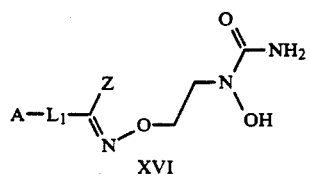

Synthesis of the Compounds

The foregoing may be better understood from the following Examples, which are presented for the purpose of illustration and not intended to limit the scope of the inventive concept as it is defined by the appended claims.

EXAMPLE 1

Preparation of 1-(benzo[b]thien-2-yl)ethyloximyl-O-2-ethyl-N-hydroxyurea

Step 1. 1-(benzo[b]thien-2-yl)ethyloximyl-O-2-ethan-1-ol.

1-(benzo[b]thien-2-yl)ethyloxime, prepared as described in U.S. Pat. No. 4,873,259, (1.02 g, 5.75 mmol) and ethylene carbonate (10 g, 115 mmol) were combined in a three-neck flask equipped with a thermometer and a drierite-filled tube. The mixture was heated to 100° C., and $K_2CO_3$ (1.59 g, 11.5 mmol) was added. After stirring 1 hour at 100° C., the reaction mixture was cooled to ambient temperature and poured into $CH_2Cl_2$ (100 mL). The reaction mixture was filtered and washed with $CH_2Cl_2$ (100 mL). The combined filtrate was washed (10% aq HCl, $H_2O$, and brine), dried ($MgSO_4$), and concentrated in vacuo to yield a yellow/brown oil. Purification by chromatography (silica gel, 20/80 EtOAc/CCl4), gave 1-(benzo[b]thien-2-yl)ethyloximyl-O-2-ethan-1-ol (0.33 g) as an off-white solid.

Step 2. 1-(benzo[b]thien-2-yl)ethyloximyl-O-2-(N,O-di-tert-butoxycarbonyl)ethylhydroxylamine.

A solution of 1-(benzo[b]thien-2-yl)ethyloximyl-O-2-ethan-1-ol, prepared as in step 1, in THF was treated with 1.3 equivalents each of triphenylphosphine, diethylazodicarboxylate, and bis-t-butoxycarbonyl hydroxlamine and the mixture was stirred for 16 hours. The solvent was evaporated and the crude mixture purified by chromatography (silica gel, 5/95 EtOAc/hexanes), to provide 0.23 g of 1-(benzo[b]thien-2-yl)ethyloximyl-O-2-(N,O-di-tert-butoxycarbonyl)ethylhydroxylamine as a pale yellow oil.

Step 3. 1-(benzo[b]thien-2-yl)ethyloximyl-O-2-ethylhydroxylamine.

To a stirred solution of 1-(benzo[b]thien-2-yl)ethyloximyl-O-2-(N,O-di-tert-butoxycarbonyl)ethylhydroxylamine (0.22 g, 0.49 mmol), prepared as in step 2, in $CH_2Cl_2$ (2.5 mL) was added trifluoroacetic acid (2.5 mL). The reaction mixture was stirred for 10 min and carefully poured into saturated aqueous $Na_2CO_3$. The mixture was extracted with ethyl acetate (3×25 mL). The combined extracts were washed (1×$H_2O$ and 1×brine), dried ($MgSO_4$), and concentrated in vacuo to yield 0.17 g of 1-(benzo[b]thien-2-yl)ethyloximyl-O-2-ethylhydroxylamine as a white solid.

Step 4. 1-(benzo[b]thien-2-yl)ethyloximyl-O-2-ethyl-N-hydroxyurea.

To a stirred THF solution of -(benzo[b]thien-2-yl)ethyloximyl-O-2-ethylhydroxylamine (0.12 g, 0.48 mmol), prepared as in step 3, was added trimethylsilyl isocyanate (0.72 mL, 4.5 mmol). The reaction mixture was stirred 0.5 hours and concentrated in vacuo. Purification by flash chromatography (silica gel, 5/95 MeOH/CH2Cl2) followed by recrystallization from ethyl acetate gave 45 mg of 1-(benzo[b]thien-2-yl)ethyloximyl-O-2-ethyl-N-hydroxyurea as a white solid. m.p. 168°–169.5° C. $^1$H NMR (300 MHz, DMSO-d6) δ2.28 (3H, s), 3.65 (2H, t, J=6 Hz), 4.27 (2H, t, J=6 Hz), 6.35 (2H, bs), 7.33–7.42 (2H, m), 7.78 (1H, s), 7.82–7.87 (1H, m), 7.88–7.93 (1H, m), 9.42 (1H, s). MS 294 (M+H)$^+$. Analysis calc'd for $C_{13}H_{15}N_3O_3S$: C, 53.23; H, 5.15; N, 14.32. Found: C, 53.01; H, 5.03; N, 14.24.

EXAMPLE 2

Preparation of hexyloximyl-O-2-ethyl-N-hydroxyurea

The desired compound was prepared according to the method of Example 1, except substituting hexanal oxime for 2-acetyl-benzo[b]thiophene oxime. Hexyloximyl-O-2-ethyl-N-hydroxyurea was purified by flash chromatography (silica gel, 3/97 MeOH, $CH_2Cl_2$) followed by recrystallization from $Et_2O$/hexanes, to provide a waxy white solid product consisting of a 58/42 mixture of oxime isomers. m.p. 65°–68° C. $^1$H NMR (300 MHz, DMSO-d6) δ0.86 (3H, t, J=7.5 Hz), 1.22–1.32 (4H, m), 1.37–1.49 (2H, m), 2.06–2.15 (1.16H, m), 2.18–2.27 (0.84H, m), 3.50–3.57 (2H, m), 4.02 (1.16H, t, J=6 Hz), 4.09 (0.84H, t, J=6 Hz), 6.28 (2H, bs), 6.73 (0.42H, t, J=6 Hz), 7.39 (0.58H, t, J=6 Hz), 9.33 (0.42H, s), 9.35 (0.58H, s). MS 218 (M+H)$^+$. Analysis calc'd for $C_9H_{19}N_3O_3$: C, 49.75; H, 8.81; N, 19.34. Found: C, 49.78; H, 8.77; N, 19.27.

EXAMPLE 3

Preparation of 1-(4-chlorobenzyl)-pyrro-2-ylmethyloximyl-O-2-ethyl-N-hydroxyurea Step 1. 1-(4-chhlorobenzyl)pyrrole-2-carboxaldehyde.

To a stirred DMSO solution of pyrrole-2-carboxaldehyde (30 g, 312 mmol) was added NaH (9.84 g, 328 mmols, 85% in an oil dispersion) slowly over a 0.5 hour period. To this stirred suspension was added 4-chlorobenzylchloride (52.8 g, 328 mmol) in DMSO (100 mL). The reaction was stirred for 10 min and saturated aqueous NH4Cl (300 mL) was added slowly. The reaction mixture was diluted with water and extracted with ethyl acetate (3×300 mL). The combined organic extracts were washed (3×brine), dried ($MgSO_4$), and concentrated in vacuo. Recrystallization from ethyl acetate/hexanes gave 60.8 g of 1-(4-chhlorobenzyl)pyrrole-2-carboxaldehyde.

Step 2. 1-(4-chlorobenzyl)pyrro-2-ylmethyloxime.

The desired compound was prepared according to the method of U.S. Pat. No. 4,873,259, except substituting 1-(4-chhlorobenzyl)-pyrrole-2-carboxaldehyde for 2-acetyl benzo[b]thiophene.

Step 3. 1-(4-chlorobenzyl)pyrro-2-ylmethyloximyl-O-2-ethan-1-ol.

The desired compound was prepared according to the method of Example 1, step 1, except substituting 1-(4-chlorobenzyl)pyrro-2-ylmethyloxime, prepared as in Step 2, for 1-(benzo[b]thien-2-yl)ethyloxime.

Step 4. 1-(4-chlorobenzyl)pyrro-2-ylmethyloximyl-O-2-ethyl-(N,O-diphenoxycarbonyl)hydroxylamine.

The desired compound was prepared according to the method of Example 1, step 2, except substituting 1-(4-chlorobenzyl)pyrro-2-ylmethyloximyl-O-2-ethan-1-ol for 1-(benzo[b]thien-2-yl)ethyloximyl-O-2-ethan-1-ol, and substituting bis-N,O-(phenoxycarbonyl)hydroxylamine for bis-t-butoxycarbonyl hydroxlamine.

Step 5. 1-(4-chlorobenzyl)-pyrro-2-ylmethyloximyl-O-2-ethyl-N-hydroxyurea.

1-(4-chlorobenzyl)pyrro-2-ylmethyloximyl-O-2-ethyl-(N,O-diphenoxycarbonyl)hydroxylamine, prepared as in step 4, was treated with NH3/MeOH. Purification by chromatography (silica gel, 2.5/97.5 and 10/90 isopropanol, ether) and recrystallization from ethyl acetate, hexanes gave 1.15 g 1-(4-chlorobenzyl)-pyrro-2-ylmethyloximyl-O-2-ethyl-N-hydroxyurea as white solid. m.p. 117.5°–118° C. $^1$H NMR (300 MHz, DMSO-d6) δ3.56 (2H, t, J = 6 Hz), 4.07 (2H, t, J = 6 Hz), 5.42 (2H, bs), 6.17 (1H, dd, J = 3 Hz, 4 Hz), 6.31 (2H, bs), 6.48 (1H, dd, J = 2 Hz, 4 Hz), 7.08–7.14 (3H, m), 7.35–7.39 (2H, m), 8.05 (1H, s), 9.38 (1H, s). MS 337 (M + H)+. Analysis calc'd for $C_{15}H_{17}ClN_4O_3$: C, 53.50; H, 5.09; N, 16.64. Found: C, 53.55; H, 5.24; N, 16.65.

EXAMPLE 4

Preparation of 3-(4-fluorophenoxy)phenylmethyloximyl-O-2-ethyl-N-hydroxyurea

The desired compound was prepared according to the method of Example 3, except substituting 3-(4-fluorophenoxy)benzaldehyde for 1-(4-chlorobenzyl)-pyrole-2-carboxaldehyde to provide 3-(4-fluorophenoxy)phenylmethyloximyl-O-2-ethyl-N-hydroxyurea as a white solid after purification by chromatography (silica gel, 3/97 MeOH, CH2Cl2 and a second column utilizing 3/97 isopropanol, Et2O) and recrystallization from EtOAc/petroleum ether. m.p. 80.3°–82.8° C. $^1$H NMR (300 MHz, DMSO-d6) δ3.62 (2H, t, J = 6 Hz), 4.21 (2H, t, J = 6 Hz), 6.31 (2H, bs), 7.01–7.06 (1H, m), 7.07–7.14 (2H, m), 7.21–7.28 (3H, m), 7.36–7.47 (2H, m), 8.23 (1H, s), 9.39 (1H, s). MS 334 (M + H)+. Analysis calc'd for $C_{16}H_{16}FN_3O_4$: C, 56.59; H, 4.96; N, 12.37. Found: C, 56.58; H, 4.61; N, 12.32.

EXAMPLE 5

Preparation of 5-(4-fluorophenoxy)fur-2-ylmethyloximyl-O-2-ethyl-N-hydroxyurea

Step 1. 2-propyloximyl-2-O-ethan-1-ol

Lithium metal (0.07 g, 10 mmol) was placed in a dry round bottom flask. The flask was fitted with a reflux condenser, and a positive N2(g) flow was maintained over the reaction. MeOH (15 mL) and EtOH (15 mL) were added. Once the metal had dissolved acetone oxime (2.0 g, 27 mmol) was added. The reaction was heated to 60° C. and ethylene oxide (2.2 mL, 46 mmol) was added. The reaction was stirred for 1 hour and additional ethylene oxide (1.0 mL) was added. After stirring an additional hour, the reaction mixture was cooled to ambient temperature, excess acetic acid was added, and the mixture was then concentrated in vacuo. The resultant orange oil was purified by chromatography (silica gel, 20/80-50/50 ethyl acetate, hexanes) to yield 2.08 g of 2-propyloximyl-2-O-ethan-1-ol as clear, colorless oil.

Step 2. O-(ethan-1-ol)hydroxylamine hydrochloride.

2-propyloximyl-2-O-ethan-1-ol, prepared as in step 1, was heated at reflux in 6N HCl for 3 hours. The reaction mixture was cooled to ambient temperature and concentrated in vacuo to yield 0.48 g of O-(ethan-1-ol)hydroxylamine hydrochloride.

Step 3. 5-(4-fluorophenoxy)fur-2-ylmethyloximyl-O-2-ethan-1-ol.

The desired compound was prepared according to the method of Example 3, step 2 except substituting 5-(4-fluorophenoxy)furan-2-carboxaldehyde (0.72 g, 3.5 mmol) for 1-(4-chhlorobenzyl)-pyrrole-2-carboxaldehyde, and substituting O-(ethan-1-ol)hydroxylamine hydrochloride (0.42 g, 3.7 mmol), prepared as in step 2 for hydroxylamine hydrochloride. Purification by chromatography (silica gel, 25/75 ethyl acetate, hexanes), provided 5-(4-fluorophenoxy)fur-2-ylmethyloximyl-O-2-ethan-1-ol (0.63 g).

Step 4. 5-(4-fluorophenoxy)fur-2-ylmethyloximyl-O-2-ethyl-N-hydroxyurea

The desired compound was prepared according to the method of Example 3, steps 4 and 5, except substituting 5-(4-fluorophenoxy)fur-2-ylmethyloximyl-O-2-ethan-1-ol, prepared as in step 3, for 1-(4-chlorobenzyl)-pyrro-2-ylmethyloximyl-O-2-ethan-1-ol. 5-(4-fluorophenoxy)fur-2-ylmethyloximyl-O-2-ethyl-N-hydroxyurea (12 mg) was obtained as a 2/1 Z/E mixture of oxime isomers after purification by chromatography (silica gel, 5/95 MeOH, CH2Cl2) and recrystallization from EtOAc/hexanes/CH2Cl2. $^1$H NMR (300 MHz, DMSO-d6) δ3.58 (0.66 H, t, J = 6 Hz), 3.67 (1.34H, t, J = 6 Hz), 4.15 (0.66H, t, J = 6 Hz), 4.26 (1.34H, t, J = 6 Hz), 5.82 (1H, d, J = 4 Hz), 6.30 (2H, bs), 6.79 (0.33H, d, J = 4 Hz), 7.20–7.33 (4.67H, m), 7.46 (0.67H, s), 8.00 (0.33H, s), 9.38 (0.33H, s), 9.42 (0.67H, s). MS 324 (M + H)+, 341 (M + NH4)+. Analysis calc'd for $C_{14}H_{14}FN_3O_5$: C, 51.30; H, 4.46; N, 12.82. Found: C, 51.23; H, 4.06; N, 12.89.

EXAMPLE 6

Preparation of 5-(4-fluorophenoxy)fur-2-ylmethyl-Z-oximyl-O-2-(1-methyl)ethyl-N-hydroxyurea Step 1. O-(1-methylethan-1-ol)hydroxylamine hydrochloride.

The desired compound was prepared according to the method of Example 5, steps 1 and 2, except substituting propylene oxide for ethylene oxide.

Step 2. 5-(4-fluorophenoxy)fur-2-ylmethyloximyl-O-2-(1-methyl)ethan-1-ol.

The desired compound was prepared according to the method of Example 5, step 3, except substituting O-(1-methylethan-1-ol)hydroxylamine hydrochloride (6.96 g, 55 mmol), prepared as in step 1, for O-(ethan-1-ol)hydroxylamine hydrochloride. Chromatography on silica gel provided Z oxime (1.33 g), and E oxime (0.89 g).

Step 3. 5-(4-fluorophenoxy)fur-2-ylmethyl-Z-oximyl-O-2-(1-methyl)ethyl-N-hydroxyurea.

The desired compound was prepared according to the method of Example 3, steps 4 and 5, except substituting 5-(4-fluorophenoxy)fur-2-ylmethyl-Z-oximyl-O-2-(1-methyl)ethan-1-ol (1.30 g, 4.66 mmol), prepared as in step 2, for 1-(4-chlorobenzyl)pyrro-2-ylmethyloximyl-O-2-ethan-1-ol. Purification by chromatography (silica gel, 2/98–2.5/97.5 MeOH, CH$_2$Cl$_2$) provided 0.87 g of 5-(4-fluorophenoxy)fur-2-ylmethyl-Z-oximyl-O-2-(1-methyl)ethyl-N-hydroxyurea. X-RAY analysis (recrystallized from MeOH/H$_2$O) indicated the Z oxime geometry. m.p. 134°–135.5° C. $^1$H NMR (300 MHz, DMSO-d6) δ1.04 (3H, d, J=6 Hz), 3.97 (1H, dd, J=6 Hz, 10.5 Hz), 4.23 (1H, dd, J=8 Hz, 10.5 Hz), 4.43–4.57 (1H, m), 5.82 (1H, d, J=4 Hz), 6.28 (2H, bs), 7.20–7.32 (5H, m), 7.43 (1H, s), 9.04 (1H, s). MS 338 (M+H)$^+$. Analysis calc'd for C$_{15}$H$_{16}$FN$_3$O$_5$: C, 53.41; H, 4.78; N, 12.46. Found: C, 53.16; H, 4.64; N, 12.31.

EXAMPLE 7

Preparation of
5-(4-fluorophenoxy)fur-2-ylmethyl-E-oximyl-O-2-(1-methyl)ethyl-N-hydroxyurea The desired compound was prepared according to the method of Example 3, steps 4 and 5, except substituting 5-(4-fluorophenoxy)fur-2-ylmethyl-E-oximyl-O-2-(1-methyl)ethan-1-ol (0.89 g, 3.2 mmol), prepared as in Example 6, step 2, for 1-(4-chlorobenzyl)pyrro-2-ylmethyloximyl-O-2-ethan-1-ol. Purification by chromatography (silica gel, 2.5/97.5 MeOH/CH$_2$Cl$_2$) provided 0.22 g of 5-(4-fluorophenoxy)fur-2-ylmethyl-E-oximyl-O-2-(1-methyl)ethyl-N-hydroxyurea. X-RAY Analysis (recrystallized from MeOH/H$_2$O) indicated the E oxime geometry. m.p. 124°–124.5° C. $^1$H NMR (300 MHz, DMSO-d6) δ0.98 (3H, t, J=6 Hz), 3.87 (1H, dd, J=6 Hz, 11 Hz), 4.10 (1H, dd, J=7.5 Hz, 11 Hz), 4.33–4.47 (1H, m), 5.80 (1H, d, J=4 Hz), 6.27 (2H, bs), 6.78 (1H, d, J=4 Hz), 7.20–7.33 (4H, m), 7.97 (1H, s), 9.02 (1H, s). MS 338 (M+H)$^+$. Analysis calc'd for C$_{15}$H$_{16}$FN$_3$O$_5$: C, 53.41; H, 4.78; N, 12.46. Found: C, 53.32; H, 4.66; N, 12.35.

EXAMPLE 8

Preparation of
5-(4-fluorophenoxy)fur-2-ylmethyl-E-oximyl-O-2-(2-methyl)ethyl-N-hydroxyurea Step 1. Ethyl-2-(1,3-dioxoindolin-2-yl)oxypropionate.

To a stirred DMF (125 mL) slurry of N-hydroxyphthalimide (20.1 g, 123 mmol) was added ethyl 2-bromopropionate (20.2 mL, 154 mmol) and triethylamine (25.8 mL, 185 mmol). The reaction mixture was stirred one hour and filtered. The filtrate was poured onto ice (800 mL) and the solid was collected and washed with H$_2$O. After recrystallization from hot EtOH, 17 g of ethyl-2-(1,3-dioxoindolin-2-yl)oxypropionate was obtained as a white powdery solid.

Step 2. 2-aminooxypropionic acid hydrobromide.

To a stirred acetic acid (55 mL) slurry of ethyl-2-(1,3-dioxoindolin-2-yl)oxypropionate was added HBr (90 mL). The solution was heated over a steambath until it became homogeneous. This material was placed in the freezer overnight and filtered. The filtrate was concentrated in vacuo. The resulting brown residue was triturated with Et$_2$O and filtered to yield 6.24 g of 2-aminooxypropionic acid hydrobromide as a solid.

Step 3. 5-(4-fluorophenoxy)fur-2-ylmethyl-E-oximyl-O-2-propionic acid.

2-aminooxypropionic acid hydrobromide (6.10 g, 32.8 mmol) and 5-(4-fluorophenoxy)furan-2-carboxaldehyde were reacted to provide the oxime isomers, 4.43 g of Compound 8.3 and 3.64 g of Compound 8.4.

The desired compound was prepared according to the method of Example 3, step 2 except substituting 5-(4-fluorophenoxy)furan-2-carboxaldehyde for 1-(4-chhlorobenzyl)-pyrrole-2-carboxaldehyde, and substituting 2-aminooxypropionic acid hydrobromide (6.10 g, 32.8 mmol), prepared as in step 2 for hydroxylamine hydrochloride. Purification by chromatography provided 5-(4-fluorophenoxy)fur-2-ylmethyl-E-oximyl-O-2-propionic acid (4.43 g), and 5-(4-fluorophenoxy)fur-2-ylmethyl-Z-oximyl-O-2-propionic acid (3.64 g).

Step 4. 5-(4-fluorophenoxy)fur-2-ylmethyl-E-oximyl-O-2-(2-methyl)ethan-1-ol.

To a 0° C. stirred CH$_2$Cl$_2$ (50 mL) solution of 5-(4-fluorophenoxy)fur-2-ylmethyl-E-oximyl-O-2-propionic acid (3.11 g, 10.6 mmol), prepared as in step 3, was added dropwise BH$_3$SMe$_2$ (1M in CH$_2$Cl$_2$, 21.5 mL, 21.5 mmol). The reaction mixture was stirred for two hours at 0° C. and one hour at ambient temperature. Methanol was added slowly and the reaction mixture was concentrated in vacuo and purified by chromatography (silica gel, 20/80–50/50 ethyl acetate, hexanes) to yield 1.19 g of 5-(4-fluorophenoxy)fur-2-ylmethyl-E-oximyl-O-2-(2-methyl)ethan-1-ol.

Step 5. 5-(4-fluorophenoxy)fur-2-ylmethyl-E-oximyl-O-2-(2-methyl)ethyl-N-hydroxyurea.

The desired compound was prepared according to the method of Example 3, steps 4 and 5, except substituting 5-(4-fluorophenoxy)fur-2-ylmethyl-E-oximyl-O-2-(2-methyl)ethan-1-ol (0.89 g, 3.2 mmol), prepared as in step 4, for 1-(4-chlorobenzyl)pyrro-2-ylmethyloximyl-O-2-ethan-1-ol. Purification by chromatography (silica gel, 2.5/97.5 MeOH, CH$_2$Cl$_2$) provided 0.24 g of 5-(4-fluorophenoxy)fur-2-ylmethyl-E-oximyl-O-2-(2-methyl)ethyl-N-hydroxyurea. X-RAY analysis (recrystallized from MeOH/H$_2$O) indicated the E oxime geometry. m.p. 107°–108.5° C. $^1$H NMR (300 MHz, DMSO-d6) δ1.19 (3H, d, J=6 Hz), 3.38 (1H, dd, J=6 Hz, 14 Hz), 3.62 (1H, dd, J=6 Hz, 14 Hz), 4.41 (1H, sextet, J=6 Hz), 5.79 (1H, d, J=4 Hz), 6.28 (2H, bs), 6.77 (1H, d, J=4 Hz), 7.18–7.33 (4H, m), 7.97 (1H, s), 9.37 (1H, s). MS 338 (M+H)$^+$, 355 (M+NH$_4$)$^+$. Analysis calc'd for C$_{15}$H$_{16}$FN$_3$O$_5$: C, 53.41; H, 4.78; N, 12.46. Found: C, 53.36; H, 4.78; N, 12.34.

EXAMPLE 9

Preparation of
5-(4-fluorophenoxy)fur-2-ylmethyl-Z-oximyl-O-2-(2-methyl)ethyl-N-hydroxyurea Step 1. 5-(4-fluorophenoxy)fur-2-ylmethyl-Z-oximyl-O-2-(2-methyl)ethan-1-ol.

To a −10° C. stirried THF (40 mL) solution of 5-(4-fluorophenoxy)fur-2-ylmethyl-Z-oximyl-O-2-propionic acid (2.95 g, 10.1 mmol), prepared as in Example 8, steps 1-3, was added triethylamine (1.5 mL, 11.1 mmol) and isobutylchloroformate (1.4 mL, 10.6 mmol). The reaction mixture was stirred for 10 min and NaBH$_4$ (1.2 g, 31.2 mmol) was added and the bath temperature raised to 0° C. After stirring 15 min, MeOH was added dropwise over two hours and the reaction mixture was then stirred overnight at ambient temperature. The reaction mixture was concentrated in vacuo, and the residue dissolved in Et$_2$O (250 mL). The ether solution was washed (1×10% aqueous HCl, 3×brine, 1×saturated aqueous NaHCO$_3$, and 1×brine), dried (MgSO$_4$), filtered, and concentrated in vacuo. Purification by chromatography (silica gel, 10/90–20/80 ethyl acetate, hexanes) yielded 0.65 g of 5-(4-fluorophenoxy)fur-2-ylmethyl-Z-oximyl-O-2-(2-methyl)ethan-1-ol.

Step 2. 5-(4-fluorophenoxy)fur-2-ylmethyl-Z-oximyl-O-2-(2-methyl)ethyl-N-hydroxyurea.

The desired compound was prepared according to the method of Example 3, steps 4 and 5, except substituting 5-(4-fluorophenoxy)fur-2-ylmethyl-Z-oximyl-O-2-(2-methyl)ethan-1-ol (0.65 g, 2.45 mmol), prepared as in step 1, for 1-(4-chlorobenzyl)pyrro-2-ylmethyloximyl-O-2-ethan-1ol. Purification by chromatography (silica gel, 2/98 MeOH, CH$_2$Cl$_2$) provided 0.17 g of 5-(4-fluorophenoxy)fur-2-ylmethyl-Z-oximyl-O-2-(2-methyl)ethyl-N-hydroxyurea. m.p. 123.5°–124.5° C. $^1$H NMR (300 MHz, DMSO-d6) δ1.23 (3H, d, J=6 Hz), 3.38 (1H, dd, J=4.5 Hz, 15 Hz), 3.82 (1H, dd, J=7 Hz, 14 Hz), 4.44–4.57 (1H, m), 5.82 (1H, d, J=3 Hz), 6.28 (2H, bs), 7.19–7.33 (5H, m), 7.46 (1H, s), 9.42 (1H, s). MS 338 (M+H)+. Analysis calc'd for C$_{15}$H$_{16}$FN$_3$O$_5$: C, 53.41; H, 4.78; N, 12.46. Found: C, 53.62; H, 4.88; N, 12.43.

EXAMPLE 10

Preparation of 5-(phenylthio)fur-2-ylmethyloximyl-O-2-ethyl-N-hydroxyurea

The desired compound was prepared as a 5:1 mixture of trans/cis isomers according to the method of Example 3 except substituting 5-thiophenoxy-2-furfuraldehyde for 1-(4-chlorobenzyl)pyrole-2-carboxaldehyde. mp: 89°–96° C. $^1$H NMR (Eoxime) (300 MHz, DMSO-d6) δ3.59 (2H,d, J=6 Hz), 4.19 (2H,d, J=6 Hz), 6.32 (2H, bs), 6.93 (1H, d, J=4 Hz), 7.08 (1H, d, J=4 Hz), 7.18–7.42 (5H, m), 8.13 (1H, s), 9.39 (1H, s). MS (DCI/NH3) m/e 339 (M+NH4)+, 322 (M+H)+, 279, 263, 204.

Additional compounds of this invention are presented in the following Table of Examples. These compounds can be prepared by converting the carbonyl intermediate shown into the desired product by the method described in Example 3.

TABLE 3

| Carbonyl Intermediate | Product |
| --- | --- |
| Example 11 | |
| Example 12 | |
| Example 13 | |
| Example 14 | |
| Example 15 | |
| Example 16 | |
| Example 17 | |
| Example 18 | |

TABLE 3-continued
| Carbonyl Intermediate | Product |
|---|---|
| 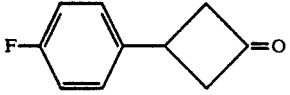 | 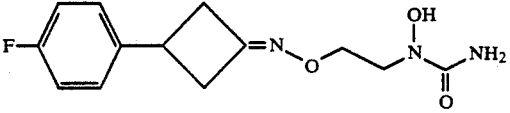 |
| Example 19 | |
| 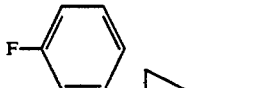 | 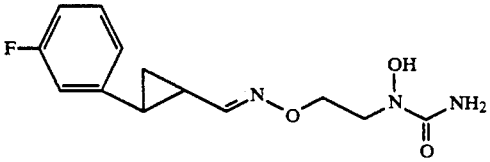 |
| Example 20 | |
| 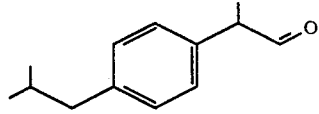 | 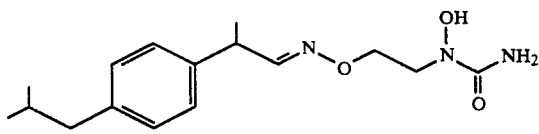 |
| Example 21 | |
| 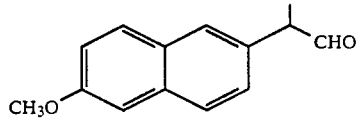 | 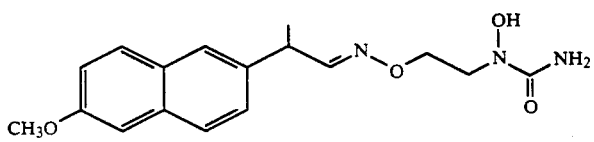 |
| Example 22 | |
| 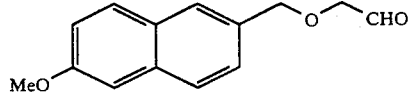 | 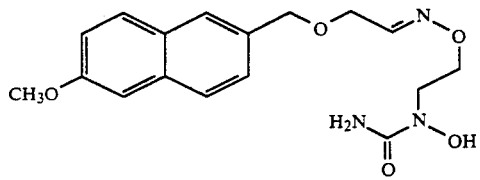 |
| Example 23 | |
| 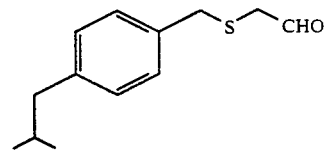 | 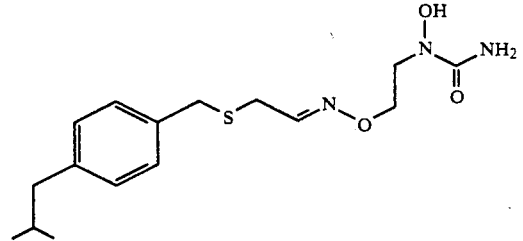 |
| Example 24 | |
| 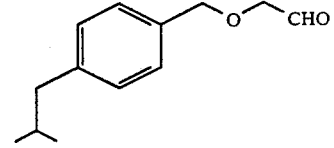 | 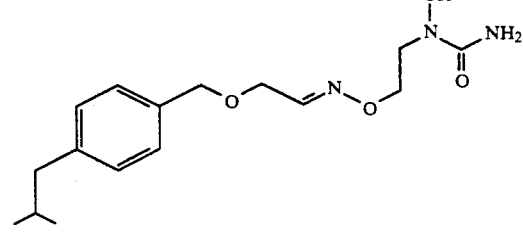 |
| Example 25 | |

TABLE 3-continued

| Carbonyl Intermediate | Product |
|---|---|
| (structure: 4-isobutylphenyl-N(Me)-CH2-CHO) | (structure: 4-isobutylphenyl-N(Me)-CH2CH2-CH=N-O-CH2CH2-N(OH)-C(=O)-NH2) |
| Example 26 (structure: 2-(2,6-dichloroanilino)phenyl-CH(CH3)-CH2-O-CH2-CHO) | (structure: corresponding oxime urea product) |
| Example 27 EtO-C6H4-CHO | EtO-C6H4-CH=N-O-CH2CH2-N(OH)-C(=O)-NH2 |
| Example 28 iBuO-C6H4-CHO | iBuO-C6H4-CH=N-O-CH2CH2-N(OH)-C(=O)-NH2 |
| Example 29 4-PhCH2O-3-MeO-C6H3-CHO | 4-PhCH2O-3-MeO-C6H3-CH=N-O-CH2CH2-N(OH)-C(=O)-NH2 |
| Example 30 4-CH3O-3-Br-C6H3-CHO | 4-CH3O-3-Br-C6H3-CH=N-O-CH2CH2-N(OH)-C(=O)-NH2 |
| Example 31 (structure: 4-MeO-C6H4-CH(CH3)-O-C6H4-CHO) | (structure: corresponding oxime urea product) |

TABLE 3-continued
| Carbonyl Intermediate | Product |
|---|---|
| Example 32 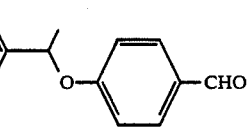 | 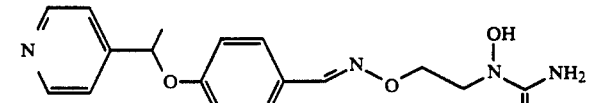 |
| Example 33  |  |
| Example 34 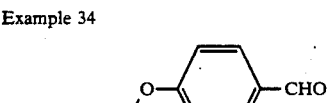 | 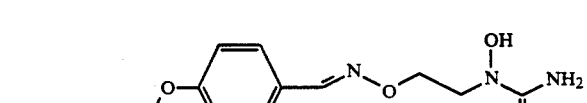 |
| Example 35  |  |
| Example 36 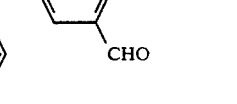 | 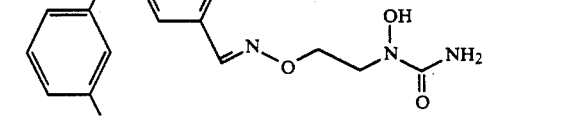 |
| Example 37 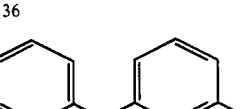 | 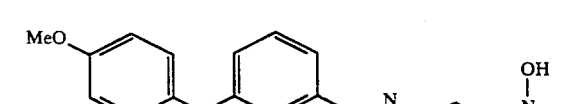 |
| Example 38 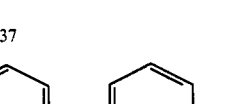 | 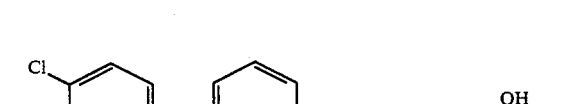 |
| Example 39  |  |
| Example 40 | |

TABLE 3-continued

| Carbonyl Intermediate | Product |
|---|---|
| 4-bromobenzaldehyde | 4-Br-C₆H₄-CH=N-O-CH₂CH₂-N(OH)-C(O)-NH₂ |
| Example 41 | |
| 4-isobutylbenzaldehyde | 4-iBu-C₆H₄-CH=N-O-CH₂CH₂-N(OH)-C(O)-NH₂ |
| Example 42 | |
| 4-phenylbenzaldehyde | 4-Ph-C₆H₄-CH=N-O-CH₂CH₂-N(OH)-C(O)-NH₂ |
| Example 43 | |
| 3-(2-thienyloxy)benzaldehyde | 3-(2-thienyloxy)-C₆H₄-CH=N-O-CH₂CH₂-N(OH)-C(O)-NH₂ |
| Example 44 | |
| 2-furaldehyde | (2-furyl)-CH=N-O-CH₂CH₂-N(OH)-C(O)-NH₂ |
| Example 45 | |
| 3-furaldehyde | (3-furyl)-CH=N-O-CH₂CH₂-N(OH)-C(O)-NH₂ |
| Example 46 | |
| 5-bromo-2-furaldehyde | (5-Br-2-furyl)-CH=N-O-CH₂CH₂-N(OH)-C(O)-NH₂ |
| Example 47 | |
| 5-phenyl-2-furaldehyde | (5-Ph-2-furyl)-CH=N-O-CH₂CH₂-N(OH)-C(O)-NH₂ |
| Example 48 | |
| 5-(2,4-difluorophenyl)-2-furaldehyde | 5-(2,4-F₂-C₆H₃)-2-furyl-CH=N-O-CH₂CH₂-N(OH)-C(O)-NH₂ |
| Example 49 | |

TABLE 3-continued

| Carbonyl Intermediate | Product |
|---|---|
| Example 50 (3-pyridyl furan CHO) | (3-pyridyl furan CH=N-O-CH₂CH₂-N(OH)-C(O)-NH₂) |
| Example 51 (EtOCH₂-furan-CHO) | (EtOCH₂-furan-CH=N-O-CH₂CH₂-N(OH)-C(O)-NH₂) |
| Example 52 (4-F-benzyl-thiophene-CHO) | (4-F-benzyl-thiophene-CH=N-O-CH₂CH₂-N(OH)-C(O)-NH₂) |
| Example 52 (4-F-benzyl-furan-CHO) | (4-F-benzyl-furan-CH=N-O-CH₂CH₂-N(OH)-C(O)-NH₂) |

We claim:

1. A compound having the structure

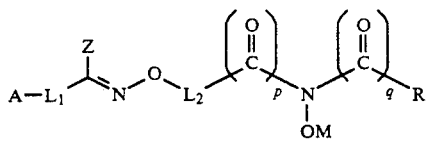

or a pharmaceutically acceptable salt thereof wherein
M is selected from the group consisting of
 hydrogen,
 a pharmaceutically acceptable cation, and
 a pharmaceutically acceptable metabolically cleavable group;
p is zero and q is one, and R is selected from the group consisting of
 hydrogen,
 alkyl of from one to twelve carbon atoms,
 cycloalkyl of from three to eight carbon atoms, and —NR₁R₂ wherein
  R₁ is selected from the group consisting of
   hydrogen,
   alkyl of from one to six carbon atoms,
   hydroxyalkyl of from one to six carbon atoms, and
   alkoxyalkyl in which the alkoxy portion and the alkyl portion each contain, independently, from one to six carbon atoms; and
  R₂ is selected from the group
   consisting of
   hydrogen,
   hydroxy,
   alkyl of from one to six carbon atoms.
   hydroxyalkyl of from one to six carbon atoms,
   alkoxyalkyl in which the alkoxy portion and the alkyl
   portion each contain, independently, from one to six carbon atoms,
   alkanoyl of from two to eight carbon atoms,
   alkyl(carbocyclic aryl) in which the alkyl portion
   contains from one to six carbon atoms, and optionally substituted (carbocyclic aryl);
L₁ is a direct bond or is selected from the group consisting of
 alkyl of from one to six carbon atoms,
 alkylenyl, of from one to six carbon atoms, and
 alkynyl of from two to six carbon atoms;
L₂ is a direct bond or is alkyl of from one to six carbon atoms;
Z is selected from the group consisting of
 hydrogen,
 alkyl of from one to six carbon atoms, and
 halosubstituted alkyl of from one to six carbon atoms;
A is selected from the group consisting of
 (a) optionally substituted thienyl; and
 (b) optionally substituted furanyl;
wherein the optional substituents are selected from the group consisting of
 (1) alkyl of from one to six carbon atoms,
 (2) haloalkyl of from one to six carbon atoms,
 (3) alkoxy of from one to twelve carbon atoms,
 (4) halogen;
 (5) phenyl or naphthyl, optionally substituted with
  alkyl of from one to six carbon atoms,
  haloalkyl of from one to six carbon atoms,
  alkoxy of from one to six carbon atoms,
  halogen;

(6) phenoxy or naphthyloxy, optionally substituted with
   alkyl of from one to six carbon atoms,
   haloalkyl of from one to six carbon atoms,
   alkoxy of from one to six carbon atoms,
   halogen;
(7) phenylthio, optionally substituted with
   alkyl of from one to six carbon atoms,
   haloalkyl of from one to six carbon atoms,
   alkoxy of from one to six carbon atoms,
   halogen;
(8) phenylalkyl, where the alkyl contains from one to six
   carbon atoms, and the phenyl group is optionally substituted with
     alkyl of from one to six carbon atoms,
     haloalkyl of from one to six carbon atoms,
     alkoxy of from one to six carbon atoms,
     halogen.

2. A compound as defined by claim 1 selected from the group consisting of
   5-(4-fluorophenoxy)fur-2-ylmethyl-Z-oximyl-O-2-(1-methyl)ethyl-N-hydroxyurea;
   5-(4-fluorophenoxy)fur-2-ylmethyl-E-oximyl-O-2-(1-methyl)ethyl-N-hydroxyurea;
   5-(4-fluorophenoxy)fur-2-ylmethyl-E-oximyl-O-2-(2-methyl)ethyl-N-hydroxyurea;
   5-(4-fluorophenoxy)fur-2-ylmethyl-Z-oximyl-O-2-(2-methyl)ethyl-N-hydroxyurea.

3. A pharmaceutical composition for inhibiting lipoxygenase enzyme activity comprising a therapeutically effective amount of a compound as defined by claim 1 in combination with a pharmaceutically acceptable carrier.

4. A method of inhibiting lipoxygenase enzyme activity in a mammal in need of such treatment comprising administering to said mammal a therapeutically effective amount of a compound as defined by claim 1.

* * * * *